United States Patent [19]
Paulik et al.

[11] Patent Number: 4,812,051
[45] Date of Patent: Mar. 14, 1989

[54] APPARATUS FOR INVESTIGATING THERMAL TRANSFORMATIONS

[75] Inventors: Jenö Paulik; Ferenc Paulik; Miklós Arnold, all of Budapest, Hungary

[73] Assignee: Magyar Optikai Muvek, Hungary

[21] Appl. No.: 857,716

[22] Filed: Apr. 30, 1986

[30] Foreign Application Priority Data

May 10, 1985 [HU] Hungary .............................. 1766/85

[51] Int. Cl.$^4$ .................. G01N 25/00; G01K 1/14
[52] U.S. Cl. ........................... 374/10; 266/99; 318/472
[58] Field of Search ............... 374/10, 11, 12, 13, 374/16, 25, 32, 33; 250/352

[56] References Cited

U.S. PATENT DOCUMENTS

| | | | |
|---|---|---|---|
| 1,285,920 | 11/1918 | Brown | 374/10 |
| 3,283,560 | 11/1966 | Harden et al. | 374/11 |
| 3,319,456 | 5/1967 | Speros et al. | 374/11 |
| 3,344,654 | 10/1967 | Erdey et al. | 374/14 |
| 3,360,993 | 1/1968 | MacMillan | 374/10 X |
| 3,524,340 | 8/1970 | Krakovetsky-Kocherzhinsky | 374/13 |

FOREIGN PATENT DOCUMENTS

| | | | |
|---|---|---|---|
| 0152197 | 2/1965 | Hungary . | |
| 0549718 | 5/1977 | U.S.S.R. | 374/10 |
| 1063898 | 4/1969 | United Kingdom . | |

OTHER PUBLICATIONS

"Differential Thermal Analysis", Ralph H. Muller, Analytical Chemistry, vol. 35, No. 4, Apr. 1963, (103A) (2 pages).

Primary Examiner—Daniel M. Yasich
Attorney, Agent, or Firm—Handal & Morofsky

[57] ABSTRACT

A temperature controlling system for investigating thermal transformation having a program-controller operated furnace the temperature of which is changed with a predetermined speed, and into which a sample and a reference substance containing elements with identical thermal parameters are placed. The sample and the reference substance containing elements are coupled with temperature sensing elements detecting their temperature and both elements are connected to a temperature comparing unit forming the difference of the two temperatures. The output of the temperature comparing unit is coupled through a differentiating network, limit switches and an actuating unit with a quasi-static temperature input of the program controller.

6 Claims, 6 Drawing Sheets

APPARATUS FOR INVESTIGATING THERMAL TRANSFORMATIONS

FIELD AND BACKGROUND OF THE INVENTION

The invention relates to a apparatus for investigating thermal transformation and to a quasi-static temperature control system for the investigation of phase transformations using a differential thermal analyser (DTA) or differential scanning calorimeter (DSC). Quasi-static temperature means that the temperature is increases continuously until thermal transformation has taken place, or conversely it means that the transformation should proceed at the same temperature under static circumstances.

Chemical and physical changes taking place as a consequence of heating involve the change of enthalpy that results in a variation of temperature of the investigated sample different from that of the ambiency. Differential thermal analyzers (DTA) have been used for the investigation of such processes for almost a century. Recently differential scanning calorimeters (DSC) are also used for the same purposes.

The DTA apparatus operates by measuring the difference between the temperature of a sample in a sample containerette and of a reference substance with similar thermal parameters. A temperature difference will only appear when the transformation in the sample begins, that is, a change of enthalpy takes place in the sample. During the investigation, both the sample and the reference substance are placed in a furnace, the temperature of which is increased with a predetermined speed by a program-controller and the temperature of sample and of reference substance as well as the difference of temperature between them is being measured and recorded. Nevertheless the, known DTA apparatus do not permit the determination characteristic temperatures belonging to individual transformations with due accuracy, which would be of very great imprtance with respect of identification of the transformation, since the temperature of the furnace grows continuously and thus the transformation takes place in a relatively wider range of temperature.

Our intention by means of the invention has been to work out a method to investigate thermal transformation and a quasi-static temperature controlling system for the investigation of phase transformations, where the phase transformation itself, controlling the temperature of the furnace, stop the increase of temperature from its beginning up to its coming to an end. At the same time the phase transformation itself ensures that the difference between the temperature of the sample and of the furnace may only be so high at which the sample may take up an amount of heat from the furnace necessary to a uniform and very low speed phase transformation.

The structure of the temperature-controller is based on the recognition that the difference of temperature appearing between the temperature of the sample and of the reference substance at the beginning of the phase transformation can be converted by a suitable converter into an electric control signal which can be used to interfere in the heating circuit of the furnace and to stop the increase of temperature. It has been recognized that said difference of temperature, since it appears at the beginning of the transformation, provides a possibility to interfere in the heating circuit of the furnace only at the beginning of the phase transformation.

Figure 1:
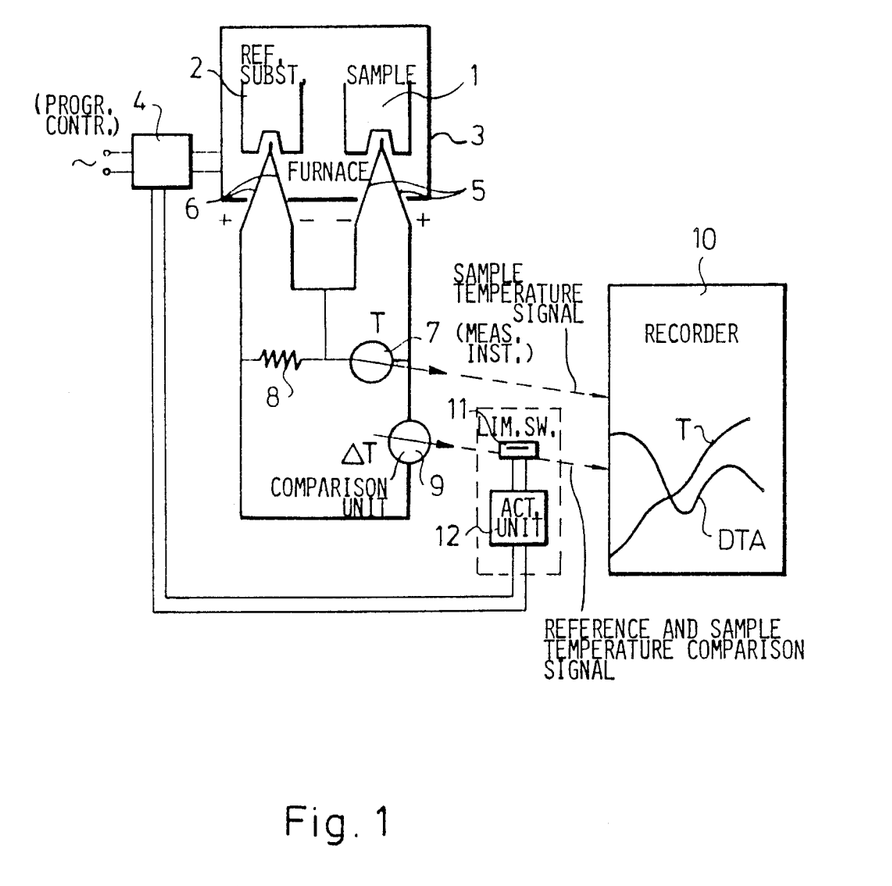
FIG. 1 shows a schematic diagram of a DTA apparatus

In order that the recognition of the present invention may clearly be explained, previous solutions will be introduced somewhat more thoroughly. FIG. 1 shows among others a DTA apparatus as well as schematically a DTA-curve received thereby, FIG. 2 shows a DTA-curve. The known DTA apparatus comprises a furnace 3 the temperature of which is increased with a predetermined and uniform speed by a program-controller 4. A sample 1 and a reference substance 2 is placed in the furnace 3. Temperature of the sample 1 as well as that of the reference substance 2 are sensed by temperature sensing elements 5 and 6, respectively. The temperature sensing elements 5 and 6, which may preferably be thermocouples, are connected to each other in series opposition. The temperature sensing element 5 is coupled with a temperature measuring instrument 7 which may be e.g. a galvanometer and the signal of said instrument 7 measuring the temperature T of the sample 1 is applied to a recorder 10. The two temperature sensing elements 5 and 6 are also coupled with the recorder 10 through a temperature comparing unit 9 showing the temperature difference. The known DTA apparatus consequently comprises a furnace 3, a sample 1 and a reference substance 2, a program-controller 4, temperature sensing elements 5 and 6 as well as a temperature measuring instrument and a temperature comparing unit 9. Curves belonging to a known DTA apparatus are shown in FIG. 2 as follows:

2a—change of temperature of the reference substance 2,

2b—change of temperature of the sample 1,

2c—difference of temperature between the sample 1 and the reference substance 2 in an ideal case and in the case when there is no transformation in the sample 1. This is therefore an ideal reference or base-line line of the DTA-curve.

2d—difference of temperature of the sample 1 and that of the reference substance 2 in real case and in case when there is no transformation in the sample 1.

2e—DTA-curve indicating transformation, i.e. the signal measured at the output of the temperature comparing unit 9.

FIG. 1 shows that there is also a resistor 8 providing for the required symmetry in the measuring circuit. It is seen in FIG. 2 that the measured DTA-curve (curve 2e) shows how the reference line is displaced, i.e. how the temperature of the furnace 3 is changed also after the beginning of the transformation. The reference or base-line is the temperature value which does not change during thermal transformation. In FIG. 2, curve 2d shows that in the known DTA when thermal transformation begins the temperature is higher than when transformation has ended. The difference between the beginning and ending temperatures is the reference or base-line displacement. It is an obvious consequence that the transformations are not taking place in an ideal way but they generally end at a temperature which is 20–100 C.° higher than the real temperature of the transformation.

It is known from Hungarian Pat. No. 152 197 how a thermogravimetric curve may be plotted among isothermal circumstances. Heating is controlled by the speed of change of sample weight. Nevertheless, the displacement of the reference line does not occur in this case so that the possibility of interference is much more favourable. It appeared at first approach that a similar method can be used in case of DTA-curves plotted by a DTA apparatus such as that shown in FIG. 1 by means of a limit switch 11 and an actuating unit 12. We thought earlier that the program-controller 4 may be operated by the actuating unit 12 so that it becomes possible to interfere if the difference of temperature exceeds the threshold signal of the limit switch 11. This solution is not applicable because of the displacement of the curve 2d. There were made attempts earlier at increasing the accuracy of the temperatures of transformations.

Bean and Oliver describe a solution of this kind in UK Pat. No. 1 063 898 disclosing an electromechanical structure which prevents the speed of transformation from increasing if it exceeds a predetermined limit. They were forced to choose this limit too wide as a consequence of the above mentioned displacement of the reference line of DTA-curve. However, they did not made an attempt at eliminating the harmful effect of the reference line.

To FIG. 2 derivative functions also are shown as follows:

2f—derivative of the curve 2c, i.e. d(2c)/dt,
2g—derivative of the ideal reference line, i.e.

$$2g = d(2e)/dt,$$

2h—derivative of the displaced reference line, i.e.

$$2h = d(2d)dt.$$

In this case, however, a limit value (2i) can be predetermined and sensed by a suitable limit switch as well as kept in a narrow range.

SUMMARY OF THE INVENTION

The above explained disadvantage may be eliminated by the present invention according to which instead of the temperature difference the derivative thereof generates an actuating signal.

The temperature controlling system can be characterized in that the output of the temperature comparing unit is coupled through a differentiating network (D-element), limit switch(es) and an actuating unit with an input of the program-controller providing a quasi-static temperature.

According to one of the preferred embodiments of the temperature controlling system the furnace is the heat insulating chamber of a differential scanning calorimeter, the heating of which comprises a basic heating element and an auxiliary heating element for the sample and a further auxiliary heating element for the reference substance containing element, wherein the actuating unit is connected to the program-controller which controls the temperature of the basic heating element.

In another preferred embodiment of the invention, the temperature sensing elements are thermocouples.

In a further preferred embodiment of the invention, the temperature sensing elements are resistance thermometers.

In a further preferred embodiment of the invention, the temperature comparing unit is connected through limit switches and actuating unit to the program-controller, and the same output of the temperature comparing unit is connected through a differentiating network to the reference line compensating circuit, a further input of which is connected to the limit switch sensing the displacement of the reference-line.

In a further preferred embodiment of the invention, the input of the circuit compensating the displacement of the reference-line is a resistor connected through an amplifier to a servo motor and to closing contact of a relay and a further contact of the said relay is connected through a further relay to the limit switch, and the actuating winding of the first relay is connected through its own closing contact and through the opening contact of the other relay to a supply unit, and the servo motor is connected to the reference line compensating potentiometer.

In a further preferred embodiment of the invention, the temperature sensing elements are resistance thermometers.

BRIEF DESCRIPTION OF THE DRAWINGS

The temperature controlling system according to the invention will be further disclosed in detail by preferred embodiments with reference to the drawings, wherein FIG. 2 shows a series of curves which can be plotted by a DTA apparatus, FIG. 4 shows a DTA-curve belonging to the preferred embodiment shown is FIG. 3, FIG. 8 shows DTA-curve and derivative curves belonging to the embodiment shown in FIG. 7.

DESCRIPTION OF THE PREFERRED EMBODIMENTS

FIG. 1 shows a DTA apparatus wherein a sample 1 and a reference substance 2 placed in containerettes are in a furnace 3 and the temperature of the furnace 3 is uniformly increased with a predetermined speed by a program-controller 4. The change of temperature of the sample 1 equals the temperature change of the reference substance 2 if phase transformation does not take place. This is shown by T-curve of a recorder 10. There are also shown the temperature changes of the sample 1 and the reference substance 2 in FIG. 2 wherein curves 2a and 2b show the change of temperature of the reference substance 2 and that of the sample 1, respectively. According to FIG. 1, the temperature of the sample 1 and that of the reference substance 2 are measured by temperature sensing elements 5 and 6, respectively, which are thermocouples in the preferred embodiment. Using thermocouples is generally preferable since the processes and thermal transformations take place in a wide range of temperature, therefore PtRh-Pt thermocouples are used most often. If the phase transformation takes place in a narrower span of temperature, a resistance thermometer may also be used. The two temperature sensing elements 5 and 6 are connected in series opposition so that temperatures may simply be compared by the temperature comparing unit 9, which is a galvanometer in this embodiment. A resistor 8 is interconnected in order to provide for adequate symmetry. A temperature measuring instrument 7 is applied to measuring the temperature of the sample 1. Changes of temperatures can be observed on a recorder 10 simultaneously. Signals of galvanometers are registered on a photosensitive paper by the recorder 10 in the present example. Using the said furnace and method of recording, however, does not allow the determination of the temperature characteristic of a phase transformation with adequate accuracy as it is referred to above background. The error is the result of the program-controller 4 further increasing the temperature of the furnace 3 (curve 2a) with a uniform speed also after the beginning of phase transformations. Consequently, the processes take place in a more or less wide range of temperature rather than in an ideal way at a well-defined temperature without the change thereof. As a result of this, the transformations end at a temperature 20–100 C.° higher than the real temperature of transformation. Even if a limit switch 11 is applied, the system would not provide for a suitable control signal as a consequence of the reference line displacement. FIG. 2 shows that if the difference of temperature of the sample 1 and that of the reference substance 2 were applied to the program-controller 4 as an actuating signal, it would be possible to control only a very high temperature difference and it would not be possible to measure several components thereby.

Figure 3:
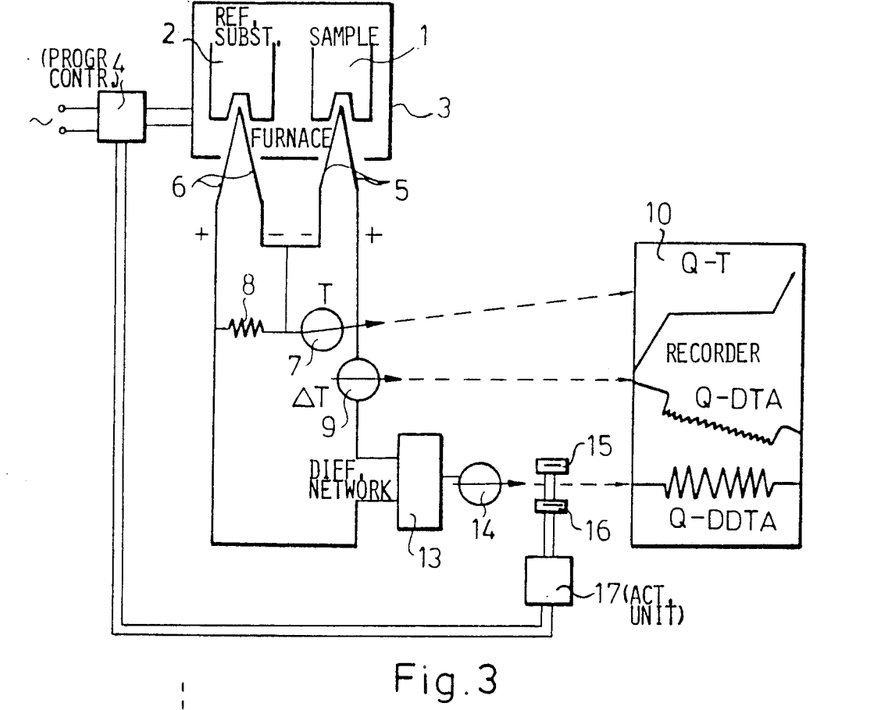
FIG. 3 shows a block diagram of a preferred embodiment of the quasi-static temperature controlling system of the invention with curves belonging thereto.

FIG. 3 shows a block diagram of an embodiment of the quasi-static temperature controlling system of the invention wherein a known DTA-curve is used as feedback actuating signal by interconnecting a differentiating network 13, limit switches 15 and 16 and an actuating unit 17 between the temperature comparing unit 9 and the program-controller 4. FIG. 4 shows temperature curves belonging to the embodiment shown as an example in FIG. 3. The curves of FIG. 4 show as follows:

4k—the temperature change of the sample as a function of time. It is well observable that the curve has a plateau i.e. the temperature of the sample is steady during transformation.

4l—reference line of a DTA-curve for an ideal case;

4m—reference line of a DTA-curve during transformation;

4n—a DTA-curve plotted in a measured case;

4o—derivative of a DTA-curve for an ideal case, i.e.

$4o = d(4m)/dt;$

4p—derivative of the displacement of the reference line, i.e.

$4p = d(4m)/dt;$

4r—derivative of a real DTA-curve, i.e.

$4r = d(4n)/dt;$ 4s and 4v denote allowable limit values designated by the limit switches 15 and 16.

Figure 5:
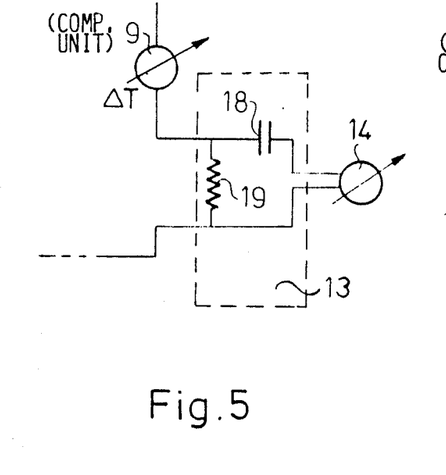
FIG. 5 shows a preferred embodiment of a differentiating network.
Figure 6:
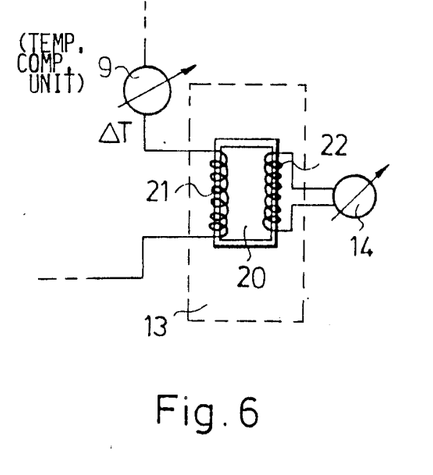
FIG. 6 shows a further preferred embodiment of the differentiating network.

Examining FIG. 4 more thoroughly reveals that even if the reference line 4m of the DTA-curve is displaced because of the asymmetry or other failure of the furnace 3 and the temperature sensing system, it results after all in a very small displacement of the derivative (curve 4p) so that the measured derivative does not fall out of hysteresis by the limit switches 15 and 16. In comparison to curve 2d of FIG. 2, line 4m indicates that the thermal transformation begins and ends at substantially the same temperature and there is, therefore, no reference or base-line displacement. According to the invention, the DTA-curve is applied to a differentiating network 13 and the output signal thereof is conducted to an actuating unit 17 through two limit switches 15 and 16, the output of the actuating unit 17 influences the heating of the furnace 3 in the program-controller 4 so that the temperature of the said furnace 3 will be kept within a prescribed limit. Since a distinct change of signal in the derivative comes into being only and exclusively at the beginning of the phase transformation, it is ensured that the phase transformation itself initiates the control and preserves it up to the end of the transformation. Each limit switch 15 and 16 is formed by a phototransistor in the preferred embodiment. The signal of the differentiating network 13 is applied to the said phototransistors through a galvanometer 14. The differentiating network 13 may be of different layout. Preferred embodiments thereof are shown by FIGS. 5 and 6. According to FIG. 5, the differentiating network 13a is a circuit arrangement comprising a resistor 19 and a capacitor 18, whereas in the preferred embodiment of FIG. 6, there is a transformer 20 forming the differentiating network 13b, the primary winding 21 of which is connected to the temperature comparing unit 9. The secondary winding 22 of the transformer is connected to the temperature measuring instrument 14. The apparatus operates as follows. A differentiating network 13 is connected to the temperature comparing unit 9 in the circuit of the known DTA apparatus for derivating the DTA-signal. The change of the derived signal is measured and indicated by the temperature measuring instrument 14 which is a galvanometer in the preferred embodiment. There are two limit switches 15 and 16, two phototransisitors according to the preferred embodiment in the path of the light signal of the galvanometer symmetrically with respect to the reference line (40). The two limit switches 15 and 16 operate the actuating unit 17 coupled with the program-controller 4.

As long as the phase transformation has not started in the sample 1, the signal of the temperature measuring instrument 14, in the preferred embodiment that of the galvanometer, is in the range between the two phototransistors and the program-controller 4 changes i.e. increases the temperature of the furnace 3 with a predetermined uniform speed (e.g. 1–10 C.°/min). When an endotherm transformation begins in the sample 1, the temperature measuring instrument puts the limit switch 16 into operation, so does the latter with the actuating unit 17 and the said actuating unit 17 changes the heating of the furnace 3 with the program-controller 4 so that it starts decreasing the heating current of the furnace 3. Consequently, the signal of the temperature measuring instrument 14 returns to a hysteresis-range defined by the limit switches 15 and 16. Temperature decreases and the transformation turns from acceleration to deceleration. This period of control takes only a few seconds and can repeat itself over and over again up to the end of transformation. After the transformation has been finished, the program-controller 4 changes the temperature of the furnace 3 again in the predetermined way.

If the transformation is exotherm instead of being endotherm, the limit switch 15 starts operating at first. Adjusting the distance of the limit switch 15 and 16 from the zero position (4s and 4v, respectively) influences the acceleration of the increase or decrease of the difference of the temperature of the sample 1 and that of reference substance 2, that is the speed of the transformation.

Figure 7:
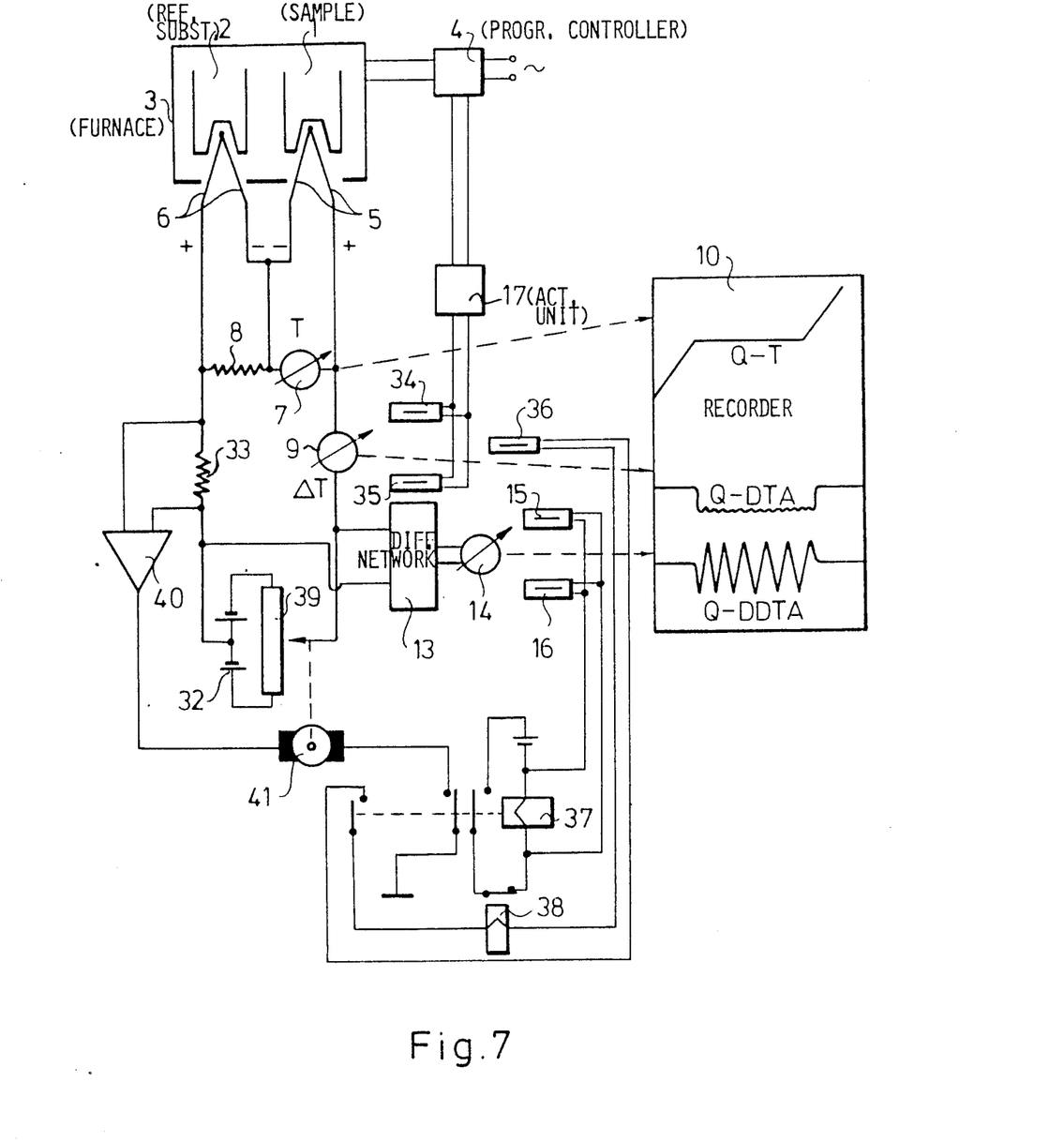
FIG. 7 shows a further embodiment of the temperature controlling system of the invention.

FIG. 7 shows another preferred embodiment of the temperature controlling system of the invention wherein the temperature comparing unit generates two signals and two pairs of limit switches 15, 16 and 34, 35 are used repectively. The actuating unit 17 is operated by the 9 temperature comparing unit a through the two limit switches 34 and 35, whereas the signal taken of the output of the differentiating network 13 is conducted to the limit switches 15 and 16. The derivative signal is used to correct reference line displacement. There are five limit switches altogether in this embodiment.

In order to understand the operation more clearly, time functions plotted in FIG. 8 may be used. FIG. 8 shows curves as follows.

8q—time variation of the temperature of the sample 1;
8t—a DTA curve where limit switch 57 indicates the temperature of transformation and limit switches 15 and 16 indicate limit values adjusting the speed of transformation;
8z—a DTA curve in the ideal and practical case, since reference line displacement is compensated here;
8w—residual reference line displacement;
8x—signal on the output of the differentiating network, that is the signal compensating reference line displacement;
8y—reference line of derivative signal.

Compensation of reference line displacement in the preferred embodiment shown in FIG. 7 is realised as follows. A resistor 33 is inserted in series in the path of output signal of the DTA-apparatus and an adjustable resistor 39, preferably a potentiometer is connected in parallel therewith. A d.c. source of voltage 32 is connected in parallel with the resistor 39. If a current flows through the resistor 33, the voltage drop thereon is applied to an amplifier 40, preferably an integrated circuit, the output of which drives a servo motor 41 moving the slide-contact of the adjustable resistor 39. Consequently, voltage difference arising between temperature sensing elements 5 and 6 connected in series opposition is automatically compensated with respect to sign and magnitude. The process of compensation continues until the beginning of transformation in the sample, i.e. up to the time when the output signal of the differentiating network 13 reaches a suitable value. The speed of transformation can be varied by adjusting the limit switches 15 and 16. A limit switch, e.g. one of the phototransistors, having been turned on switches self-holding relay 37 on. When the relay 37 is switched on, it breaks the circuit of the servo motor 41 with one of its breaking contacts, i.e. stops the servo motor 41. At the same time another making contact of the relay 37 also closes and the circuit of the limit switch 36 is adjusted precisely to the reference signal. From that instant on the compensation ceases, as a consequence of the transformation, the temperature difference between the sample 1 and of the reference substance 2 continuously increases which results in an increasing signal on the output of the temperature comparing unit 9. Hence, when the speed of transformation reaches an adjusted value, one of the limit switches starts operating and puts into operation the actuating unit 17 which then regulates the program-controller suitably. At the end of the transformation, the signal on the output of the temperature comparing unit 9 will be within the hysteresis determined by the limit switches 34 and 35. The limit switch 36 then puts into operation the relay 38 which in turn breaks for a moment the self-holding circuit of the relay 37. The making contact of the said relay 37 then closes the circuit of the servo motor 41 and the compensation will operate again. Displacement of the reference line may be in any direction since the servo motor 41 is connected to a tapped d.c. voltage source 32 so that it may compensate in both directions.

Figure 9:
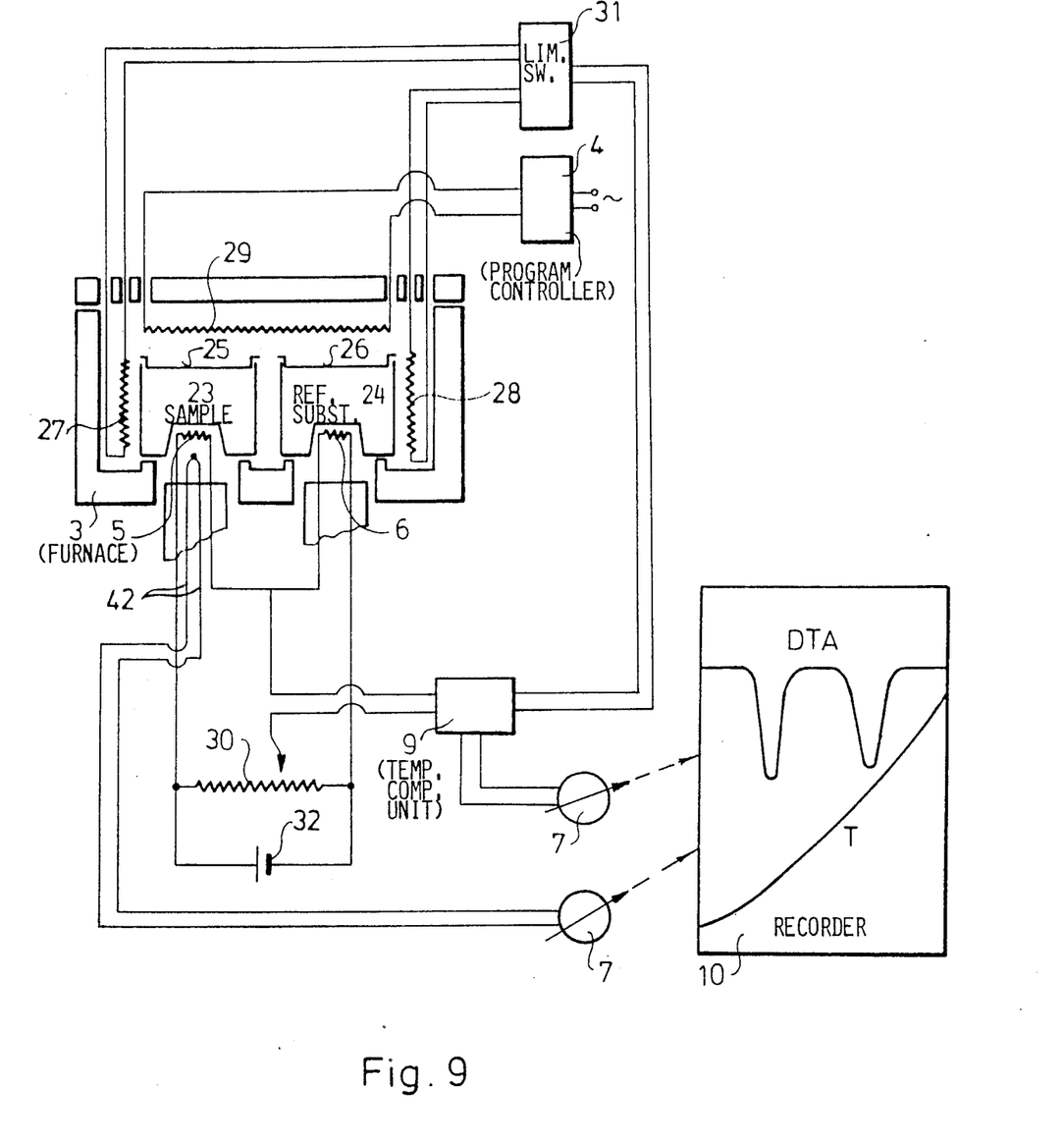
FIG. 9 shows a temperature measuring and registrating system in which a DSC is used.
Figure 10:
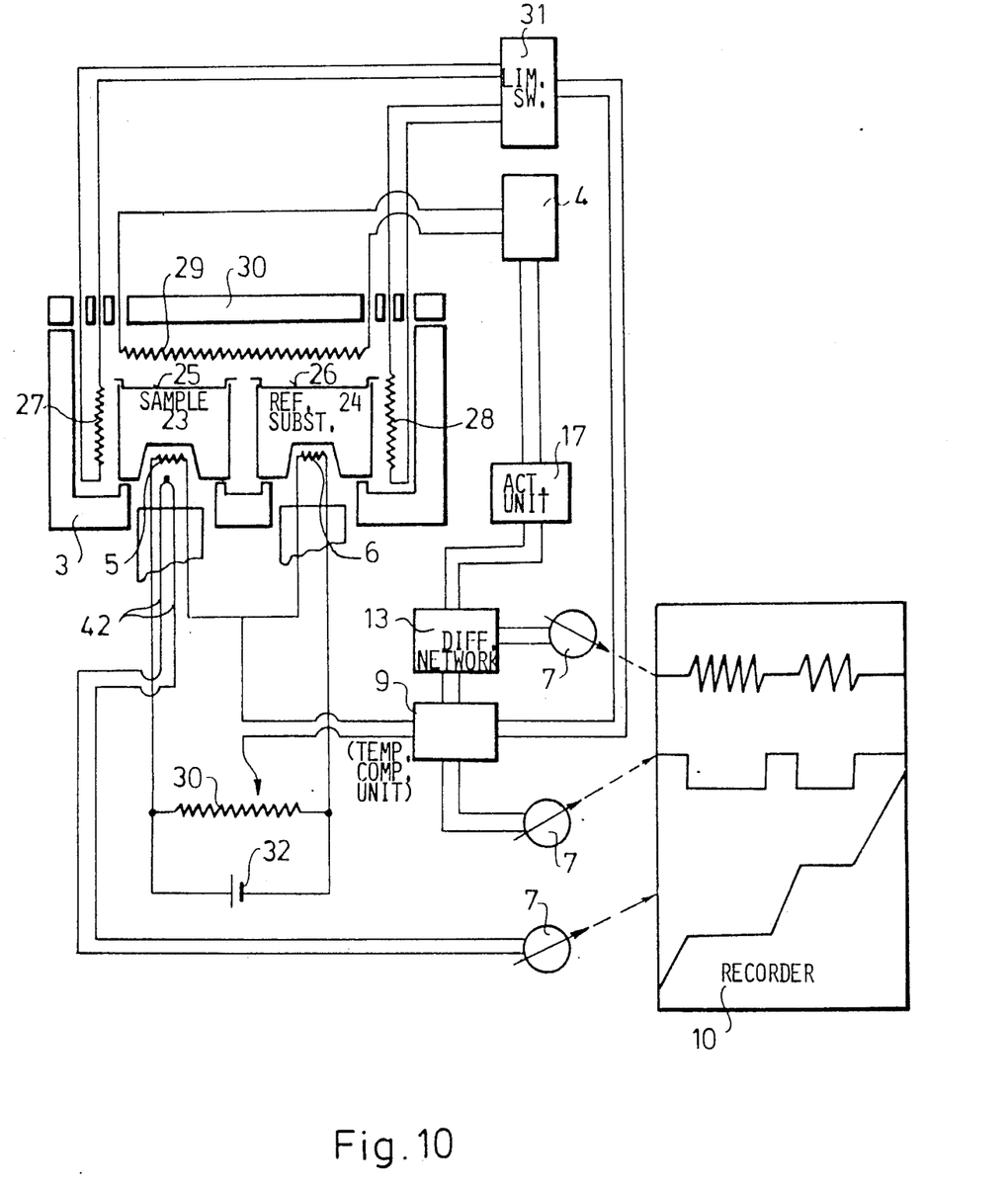
FIG. 10 is a version of the system shown in FIG. 9 improved according to the invention, FIGS. 11(a–f) on its diagrams (a)–(f); shows a two-component phase transformation with a traditional temperature control and an improved one according to the invention.

Differential scanning calorimeters (DSC) may also be used instead of a DTA apparatus for quantitatively determining the changes of enthalpy caused by transformations. FIGS. 9 and 10 show a further preferred embodiment for DSC. FIG. 9 is the known solution and FIG. 10 is the arrangement according to the invention. A DSC differs from a DTA only in that the sample containerette of the reference substance is empty in case of traditional measurements and the temperature of the sample containerette is measured instead of that of the sample. The DSC measures also the specific heat variation of the sample besides the enthalpy variation of the transformation. If a reference substance of heat capacity nearly identical with that of the sample is nevertheless placed in the sample containerette, the DSC can be used to plot a regular DTA curve. The two systems differ from each other also in that the DSC has a double heating system.

Accordingly, FIG. 9 shows the known solution wherein a sample 23 and a reference substance 24 are respectively placed in containing elements 25 and 26, enclosed by heat insulated furnace 3. The temperature of the furnace 3 is increased with uniform speed by a basic heating element 29. The speed of heating is adjusted by program-controller 4. When a transformation take place in sample 23, a temperature difference could arise between the sample 23 and the reference substance 24 or the originally empty containing element 26, respectively. The said temperature difference is nevertheless prevented from arising by auxiliary heating elements 27 or 28 operating independently of the basic heating element 29. The temperature difference is compensated by the heat dissipated by the first auxiliary heating element 27 or the second auxiliary heating element 28 in the case of endotherm transformation or exotherm transformation, respectively. Temperature of the sample 23 and of the reference substance 24 and those of the containing elements 25 and 26 respectively equal each other in every instant in actual fact. Temperature sensing elements 5 and 6 are also applied in this system, which are resistance thermometers connected in a bridge with an adjustable resistor 30 and a d.c. voltage source 32 in the preferred embodiment. The common point of the temperature sensing elements 5 and 6 and the slide-contact of the resistor 30 are connected to the temperature comparing unit 9 which is coupled with the temperature measuring instrument 7 as well as the recorder 10. The temperature of the sample 23 is measured with another thermocouple 42 and is indicated with the temperature measuring instrument and optionally the recorder 10. The output of the temperature comparing unit 9 is coupled with the auxiliary heating elements 27 and 28 through limit switch 31. Hence, the recorder 10 registers time variations of the heat dissipated by the auxiliary heating elements 27 and 28 and engaged by the sample 23 or the reference substance 24, respectively. The curve received in this way therefore substantially equals the DTA curve.

This apparatus has the advantage over a DTA apparatus in that enthalpy variation caused by transformations may be determined quantitatively more conveniently and more precisely by measuring the power of the auxiliary heating elements 27 and 28.

FIG. 10 shows a quasi-static temperature controlling system of the invention applied to DSC on the analogy of the system realized with DTA-apparatus. The output of the temperature comparing unit 9 is henceforward conducted to the limit switch 31 on the one hand, and is coupled with the program-controller 4 through a differentiating network 13 and an actuating unit 17 on the other. The temperature comparing unit 9 is coupled with the recorder 10 by means of the temperature measuring instrument 7. The signal proportional to the electric power dissipated by the auxiliary heating element 27 and 28 is received on the output of the temperature comparing unit 9. This system is also suitable for carrying out the version shown in FIG. 7, wherein the reference line displacement is compensated. Naturally, the quasi-static temperature controlling system may also be realised so that all the controlling and actuating elements are carried out by means of a microprocessor and certain units are integrated. The basic principle is the same at each version, namely the phase transformation itself should trigger an actuating signal in the program-controller 4 by means of which further temperature increase of the furnace 3 is brought to a halt.

The quasi-static temperature controlling system of the invention fundamentally changes the process of the transformations such that it makes ideal experimental circumstances for the investigations. The transformations can be studied from entirely new point of view by reason of the course of the received curve different from that known till now. Isotherm or anisotherm character of the investigated transformation can be sharply distinguished on the basis of the recorder curves. In the former case, the temperature of the sample remains constant from the beginning to the end of the transformation (see curve 4k), and in the latter case, the temperature continuously increases. The measured temperatures will be characteristic strictly of the transformation in both cases. Neither the measurement nor the evaluation will be falsified.

Figure 11:
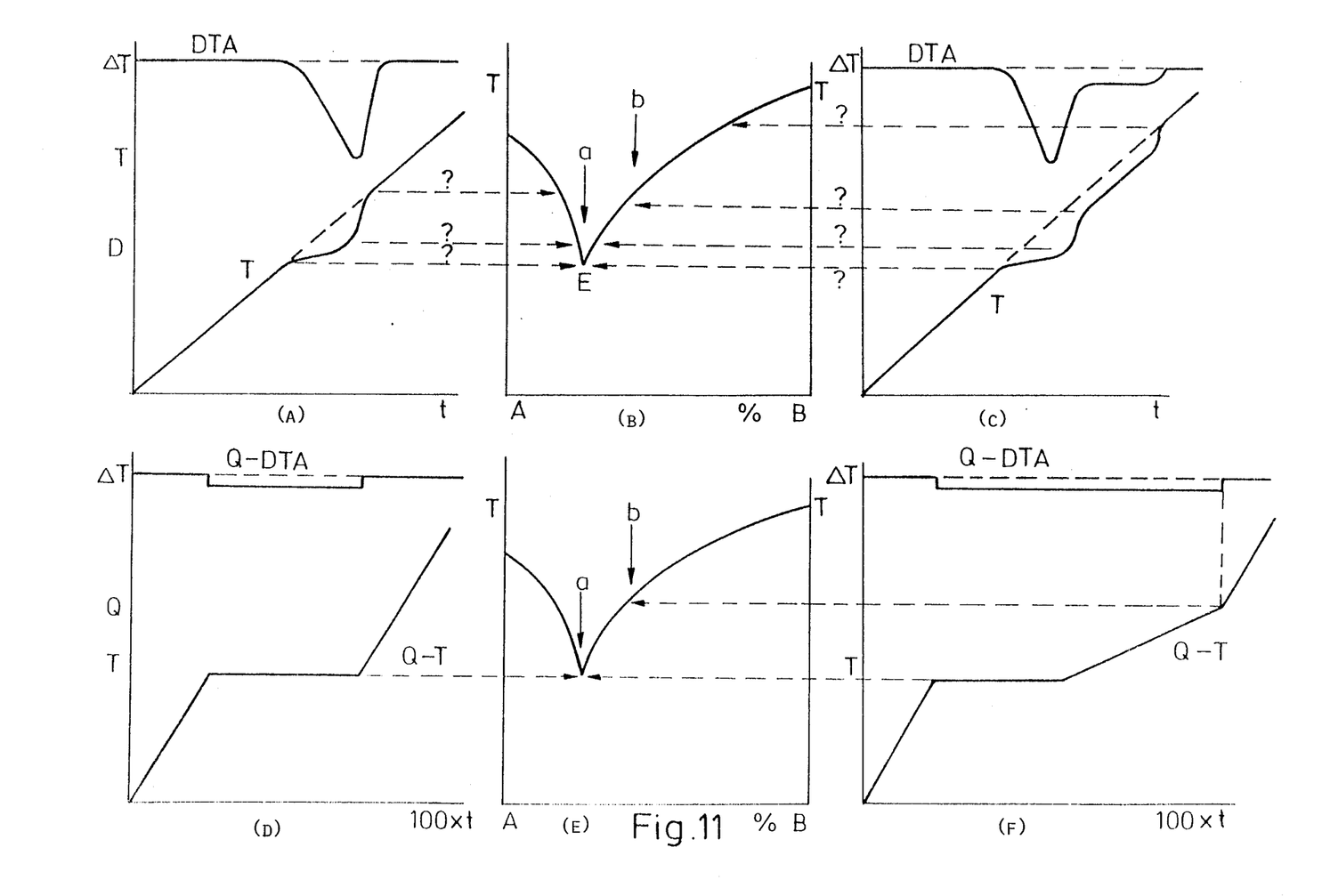

In order to support the above mentioned, FIG. 11 shows the advantages of the invention. It is shown how the phase diagram of the two-component system can be plotted by means of the known DTA curves and making use of the curve received by the system according to the invention, respectively.

The upper three diagrams (a)-(c) in FIG. 11 show curves received traditionally where the question-marks denote uncertainty of determining the precise temperature. Phase transformation, formation of eutectic compositions, of compounds, of solid solutions, change of modification may be sensible detected by DTA investigation, however, temperatures of transformations cannot be precisely determined. This occurs because the temperature of the furnace uniformly increases also after the beginning of the phase transformation and a fall of temperature arises inside the sample and therefore the process ends at a temperature far above the temperature of the transformation.

If the same phase transformation is investigated by means of the quasi-static temperature controlling system, as the lower four diagrams of FIG. 11 shows, the values of temperature which can be read off and determined will strictly correspond to the state of equilibrium. For example, in case of eutectic compositions the temperature remains constant up to the end of the transformation (FIG. 11a). In cases shown in FIG. 11b wherein solidification is initiated by the precipitation of one of the components (component A) and solidification of the eutectic (E) only follows it, the temperature variation during the first process can be precisely read off by means of curves Q and T.

Various modifications in structure and/or function may be made to the disclosed embodiments by one skilled in the art without departing from the scope of the invention as defined by the claims.

What is claimed is:

1. A temperature controlling system for investigating thermal transformations comprising:
    a furnace, operated by a program-controller, wherein the temperature in the furnace changes with a predetermined speed;
    a sample container and a reference substance container disposed in the furnace for receiving a sample and a reference substance, respectively, each container having similar thermal parameters;
    respective temperature sensing elements coupled to the sample container and the reference substance container for sensing the temperature of the sample and the reference substance;
    a temperature comparing unit connected to the sample and reference temperature sensing elements for forming a difference output signal of the temperatures, the difference output signal being an input to a recorder;
    a differentiating network means receiving as an input the difference output temperature signal for providing an output which is the derivative of the difference output temperature signal;
    limit switch means for limiting the value of the derivative output and thereby providing a quasi-static temperature signal; and
    an actuating unit having the quasi-static temperature signal as an input, the actuating unit being connected to the program-controller whereby the furnace temperature is controlled in accordance with the quasi-static temperature signal.

2. A temperature controlling system as claimed in claim 1, wherein the furnace is a heat insulating chamber of a differential scanning calorimeter, the chamber having a basic heating element, an auxiliary heating element for the sample container and a further auxiliary heating element for the reference substance container, wherein said actuating unit is connected to the program-controller for controlling the temperature of the basic heating element.

3. A temperature controlling system as claimed in claim 1, wherein the temperature sensing elements are thermocouples.

4. A temperature controlling system for investigating thermal transformation comprising:
    a furnace, operated by a program-controller, wherein the temperature increases with a predetermined speed;

a sample container and a reference container disposed in the furnace for receiving a sample and a reference substance, respectively, each container having similar thermal parameters;

respective temperature sensing elements connected to the sample container and reference substance container for sensing the temperature of the sample and the reference substance;

a temperature comparing unit connected to the sample and reference temperature sensing elements for forming a first and second difference output signal of the temperatures;

first limit switches for receiving the first temperature difference output signal and providing a limiting output;

an actuating unit having the limiting output as an input, the actuating unit being connected to the program-controller;

a differentiating network receiving as an input the second difference output signal for providing an output which is the derivative of the second difference output temperature;

a second limit switch connected to the temperature sensing elements for generating a signal representing the change in the temperature values; and a compensation circuit receiving as an input the derivative output for adjusting the signal representing the change in the respective values of the temperature sensing elements during thermal transformation.

5. A temperatue controlling system for investigating thermal transformation comprising:

a furnace, operated by a program-controller, wherein the temperature increases with a predetermined speed;

a sample container and a reference container disposed in the furnace for receiving a sample and a reference substance, respectively, each container having similar thermal parameters;

respective temperature sensing elements connected to the sample container and reference substance container for sensing the temperature of the sample and the reference substance;

a temperature comparing unit connected to the sample and reference temperature sensing elements for forming a first and second difference output signal of the temperatures;

first limit switches for receiving the first temperature difference signal output and providing a a limiting output;

an actuating unit having the limiting output as an input, the actuating unit being connected to the program-controller;

a differentiating network receiving as an input the second difference output signal for providing an output which is the derivative of the second difference output temperature;

a second limit switch connected to the temperature sensing elements for generating a signal representing the change in the temperature values; and a compensation circuit receiving as an input the derivative output for adjusting the signal representing the change in the respective values of the temperature sensing elements during thermal transformation, wherein the compensating circuit includes a resistor connected to the respective temperature sensing elements and to an amplifier, the amplifier being connected to a servo motor, the servo motor being connected to an adjusting element of a variable potentiometer, the potentiometer being connected to a first voltage supply, the first voltage supply being connected to the resistor and the amplifier; and the derivative output being connected to a first relay, the first relay having a first contact connected to the servo motor and a second contact is connected to a second relay which is actuated by the second limit switch, the first relay being self-holding through a second voltage supply and a third contact.

6. A temperature controlling system as claimed in claim 5, wherein the temperat sensing elements are resistance thermometers.

* * * * *